United States Patent [19]

West et al.

[11] Patent Number: 5,240,889
[45] Date of Patent: Aug. 31, 1993

[54] HYDRATED ALKYLATION CATALYST

[75] Inventors: Martin West, Huntington Beach; Suheil F. Abdo, Placentia, both of Calif.

[73] Assignee: Union Oil Company of California, Los Angeles, Calif.

[21] Appl. No.: 729,458

[22] Filed: Jul. 12, 1991

[51] Int. Cl.$^5$ .............. B01J 29/02; B01J 29/04; B01J 21/16

[52] U.S. Cl. .......... 502/64; 502/61; 502/63; 502/202; 502/208; 502/214; 502/242; 502/256; 502/258

[58] Field of Search .......... 502/60, 63, 64, 61, 502/202, 208, 214, 242, 256, 258

[56] References Cited

U.S. PATENT DOCUMENTS

| | | | |
|---|---|---|---|
| 3,929,672 | 12/1975 | Ward | 252/455 Z |
| 4,169,111 | 9/1979 | Wight | 585/323 |
| 4,185,040 | 1/1980 | Ward et al. | 585/467 |
| 4,459,426 | 7/1984 | Inwood et al. | 585/323 |
| 4,604,373 | 8/1986 | Clark | 502/65 |
| 4,798,816 | 1/1989 | Ratcliffe et al. | 502/62 |
| 4,849,569 | 7/1989 | Smith, Jr. | 585/446 |
| 4,876,408 | 10/1989 | Ratcliffe et al. | 585/467 |
| 4,992,606 | 2/1991 | Kushnerick et al. | 585/467 |
| 5,015,611 | 5/1991 | Clark | 502/20 |
| 5,036,033 | 7/1991 | West et al. | 502/64 |
| 5,077,445 | 12/1991 | Le | 585/467 |

FOREIGN PATENT DOCUMENTS 0064046 11/1982 European Pat. Off. .
0308099 3/1989 European Pat. Off. .

*Primary Examiner*—Carl F. Dees
*Attorney, Agent, or Firm*—Yale S. Finkle; Gregory F. Wirzbicki

[57] ABSTRACT

A composition useful for catalyzing alkylation and transalkylation reactions comprises a molecular sieve having alkylation and/or transalkylation activity, an inorganic refractory oxide component and greater than 3.5 weight percent water. Such a catalyst has been found to maintain a long life when used to produce ethylbenzene in an integrated process in which benzene is alkylated with ethylene and transalkylated with diethylbenzene. The catalyst can also be used to produce cumene via an integrated process in which benzene is alkylated with propylene and transalkylated with diisopropylbenzene.

50 Claims, 2 Drawing Sheets

HYDRATED ALKYLATION CATALYST

BACKGROUND OF THE INVENTION

This invention relates to alkylation and transalkylation processes and catalysts for use therein. The invention is particularly concerned with catalysts having an initial content of water sufficiently high to decrease catalyst deactivation by inhibiting reactant decomposition during the start-up of such processes, thereby significantly increasing the life of the catalysts.

In the past it has been common practice to alkylate aromatic molecules such as benzene, toluene and xylene with ethylene, propylene and other olefins using acidic homogeneous Friedel-Crafts type catalysts such as aluminum halides or heterogeneous acidic silica-alumina catalysts. Such processes have several disadvantages including corrosion problems caused by some of the catalysts and difficulty in controlling the product distribution obtained from the alkylation reactions. Often, the desired product is the monoalkylate rather than the di- or trialkylate. In an effort to avoid a large production of di- and trialkylate products and to extend catalyst life, it is conventional practice to use a large excess of the aromatic compound.

To avoid some of the problems associated with earlier commercial alkylation processes, solid zeolite-containing catalysts have been used in recent years to promote the alkylation of aromatic compounds with olefins and other alkylating agents, especially the alkylation of benzene with ethylene. Such zeolite-containing catalysts are normally prepared by combining a zeolite with a refractory oxide binder or precursor thereof, mulling and extruding the mixture, drying the extrudates and then calcining the dried extrudates at high temperatures to provide the extrudates with the strength required to withstand commercial operations. Naturally occurring and synthetic zeolites typically contain a relatively large concentration of sodium ions and are therefore not catalytically active. Thus, before a zeolite is mixed with the refractory oxide component or precursor thereof in the manufacturing of a zeolite-based catalyst, the zeolite is normally subjected to ion exchange, typically with ammonium ions, to reduce its sodium concentration as low as practically possible and increase its catalytic activity. However, since ammonia is known to poison the acid sites of the zeolite, it is common practice to carry out the calcination of the dried extrudates at such temperatures that substantially all of the ammonium ions in the catalyst are decomposed into hydrogen ions and ammonia which is driven out of the catalyst as a gas. The use of such calcination temperatures also drives off substantially all of the water present anzeolite-based typically results in a substantially dry catalyst.

Normally, zeolite-based alkylation catalysts prepared as described above are used in fixed bed reactors through which the reactants are continuously passed. Although such fixed bed processes using zeolite-containing catalysts have advantages over earlier commercial processes, the life and deactivation rate of the catalysts, especially when used to produce ethylbenzene by reacting ethylene with benzene, have been observed in pilot plant studies to vary from one catalyst to another with the life of some of the catalysts being so low that commercial processes using such catalysts would be uneconomical.

Accordingly, there is a need for zeolite-containing catalysts that do not readily deactivate when used to catalyze alkylation and transalkylation reactions, and therefore consistently maintain a relatively long life.

SUMMARY OF THE INVENTION

In accordance with the invention, it has now been surprisingly found that the life of catalysts comprising an inorganic refractory oxide component and a crystalline molecular sieve in alkylation and transalkylation processes is dependent on the water content of the catalyst. It has been further found, contrary to what is commonly believed in the art, that it is most desirable to maintain a minimum level of water in such catalysts during process start-up to avoid substantial decomposition of the first reactant introduced into the alkylation or transalkylation reactor as the temperature in the reaction zone is increased to alkylation and/or transalkylation temperatures. It has been found that this minimum level is typically equal to or greater than the equilibrium amount of water the catalyst would contain at any temperature during the start-up procedure that is greater than the temperature at which the first introduced reactant begins to decompose. Normally, this minimum level of water is greater than 3.5 weight percent of the catalyst and generally ranges between about 4.0 and 25 weight percent. Accordingly, the invention is directed to a catalyst composition of long life which, in its broadest embodiment, contains a molecular sieve and at least about 3.5 weight percent water based on the total weight of the catalyst. Preferably, the molecular sieve used in preparing the catalyst is a steam-stabilized, modified Y zeolite. The level of water in the catalyst typically ranges between about 4.0 and 25 weight percent, preferably between about 5.0 and about 15 weight percent. All water contents referred to herein are calculated by measuring weight loss on ignition (LOI), which is normally determined by calculating the weight loss after heating at 1000° C. for two hours, and then subtracting the amount of weight loss due to ammonium ion decomposition into ammonia.

The catalyst of the invention is typically prepared by exchanging a molecular sieve with ammonium ions, mixing the resultant ion-exchanged sieve with a porous, inorganic refractory oxide component or precursor thereof, extruding the resultant mixture to form extrudates, drying the extrudates, calcining the dried extrudates, and then hydrating the calcined extrudates so they contain water in amounts above the minimum level of 3.5 weight percent. As used herein, "extruding" includes all forms of pelleting including tableting, extruding, prilling and the like. Alternatively, if it is desired to use the catalyst in a fluidized bed reactor, a slurry of the ammonium-exchanged molecular sieve and refractory oxide component can be prepared, spray-dried to produce particles which typically range between 40 and 80 microns in diameter and then hydrated to the desired water content.

Catalysts of the invention have been found to resist deactivation during process start up and thereby possess relatively long lives when used in a variety of alkylation and transalkylation processes in which an organic feedstock is contacted with an organic reactant to form an alkylated organic compound in the presence of such catalysts. In one specific embodiment of the process of the invention, the catalyst of the invention is employed in the alkylation zone of a process for producing ethylbenzene via the alkylation of benzene with ethylene and may also be employed downstream in the process in a transalkylation zone wherein benzene is subjected to transalkylation by contacting it with diethylbenzene, an undesired by-product of the reaction between benzene and ethylene, to produce additional quantities of ethylbenzene. The use of a long-life catalyst of the invention in such a process can substantially reduce capital investment and operating costs by enabling less catalyst to be used in smaller alkylation and reactors, and decreasing the number of times catalyst must be regenerated.

DETAILED DESCRIPTION OF THE INVENTION

Figure 1:
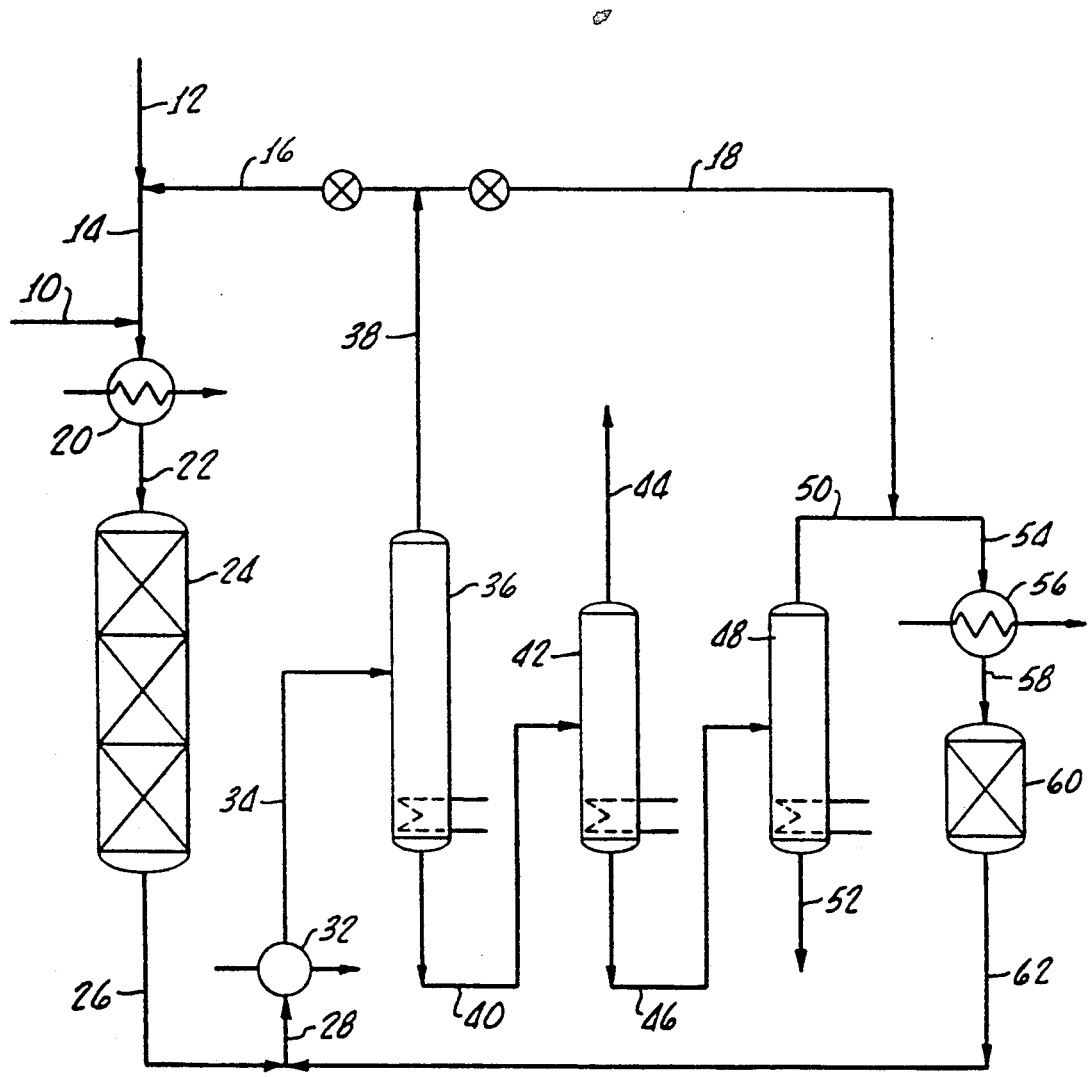
FIG. 1 in the drawing is a schematic flow diagram of a process for producing cumene or ethylbenzene utilizing both alk transalkylation reactors containing the catal of the invention.

The molecular sieve-containing catalyst of the invention, which is typically free of hydrogenation metal components, comprises a crystalline zeolitic or nonzeolitic molecular sieve composited with a porous, inorganic refractory oxide matrix or binder. The term "molecular sieve" as used herein refers to any material capable of separating atoms or molecules based on their dimensions. The term "nonzeolitic" as used herein refers to molecular sieves whose frameworks are not formed of substantially only silicon and aluminum atoms in tetrahedral coordination with oxygen atoms whereas the term "zeolitic" as used herein refers to molecular sieves whose frameworks are formed of substantially only silicon and aluminum atoms in tetrahedral coordination with oxygen atoms, such as the framework present in ZSM-5 type zeolites, Y zeolites, and X zeolites. Examples of nonzeolitic, crystalline molecular sieves which may serve as the active alkylation or transalkylation component of the catalyst include silicoaluminophosphates, metalloaluminophosphates, titanium silicates, galliosilicates, ferrosilicates, chromosilicates, borosilicates, pillared clays, delaminated clays and crystalline silicas such as silicalite. Several of these nonzeolitic molecular sieves are discussed in more detail in U.S. Pat. Nos. 4,867,861 and 4,829,040, the disclosures of which are hereby incorporated by reference in their entireties. Examples of zeolitic, crystalline molecular sieves which may be used as the active alkylation or transalkylation component of the catalyst include those selected from the group of Y zeolites, fluorided Y zeolites, X zeolites, zeolite beta, zeolite L, zeolite omega, mordenite and modifications of such zeolites. It is preferred that the crystalline molecular sieve used in the catalyst of the invention have a Constraint Index below about 1.0 and pores defined by 12-membered rings of oxygen atoms, i.e., a pore size greater than 7.0 angstroms.

The preferred molecular sieves for use in the catalyst of the invention are Y zeolites and modified Y zeolites. U.S. Pat. No. 3,130,007, the disclosure of which is hereby incorporated by reference in its entirety, describes Y-type zeolites having an overall silica-to-alumina mole ratio between about 3.0 and about 6.0, with a typical Y zeolite having an overall silica-to-alumina mole ratio of about 5.0.

The modified Y zeolites suitable for use in preparing the catalyst of the invention are generally derived from Y zeolites by treatment which results in a significant modification of the Y zeolite framework structure and composition, usually an increase in the framework silica-to-alumina mole ratio to a value typically above 6.0, and/or a reduction in unit cell size. It will be understood, however, that, in converting a Y zeolite starting material to a modified Y zeolite useful in the present invention, the resulting modified Y zeolite may not have exactly the same X-ray powder diffraction pattern for Y zeolites as is disclosed in U.S. Pat. No. 3,130,007. The d-spacings may be shifted somewhat due to a shrinkage in the unit cell size caused by an increase in the framework silica-to-alumina mole ratio. The essential crystal structure of the Y zeolite will, however, be retained so that the essential X-ray powder diffraction pattern of the modified zeolite used in the catalyst will be consistent with that of either Y zeolite itself or a Y zeolite of reduced unit cell size. Examples of modified Y zeolites that can be used in preparing the catalyst of the invention include steam-stabilized Y zeolites, dealuminated Y zeolites and ultrahydrophobic Y zeolites.

Steam-stabilized Y zeolites are Y zeolites which have been hydrothermally treated to increase their framework silica-to-alumina mole ratio with only a small increase in their overall silica-to-alumina mole ratio. Steam stabilization normally involves calcination of the ammonium or hydrogen form of the Y zeolite starting material at relatively high temperatures, typically above about 900° F., in the presence of steam. This treatment results in the expulsion of tetrahedral aluminum from framework into nonframework positions, but normally does not remove the aluminum from the zeolite and therefore does not significantly increase the overall silica-to-alumina mole ratio of the starting Y zeolite.

A preferred steam-stabilized Y zeolite for use as the starting molecular sieve in preparing the catalyst of the invention is one produced by (1) ammonium exchanging a Y zeolite to a sodium content between about 0.6 and 5 weight percent, calculated as $Na_2O$, (2) calcining the ammonium-exchanged zeolite at a temperature between about 600° F. and 1650° F. in the presence of steam at a water vapor partial pressure of at least 0.2 p.s.i.a., preferably above about 2.0 p.s.i.a., and most preferably between about 5.0 and 15 p.s.i.a., to reduce the unit cell size of the ammonium-exchanged zeolite to a value in the range between about 24.35 and about 24.65 angstroms, preferably between about 24.40 and 24.64 angstroms, and then (3) ammonium exchanging the steam calcined zeolite to replace at least 25 percent of the residual sodium ions and obtain a zeolite product containing less than about 1.0 weight percent sodium, preferably less than about 0.6 weight percent sodium, and most preferably below about 0.2 weight percent sodium, calculated as $Na_2O$. Such a Y zeolite is highly stable and maintains a high activity. The zeolite is described in detail in U.S. Pat. No. 3,929,672, the disclosure of which is hereby incorporated by reference in its entirety.

The preferred steam-stabilized Y zeolites, whether produced by the process described above or steam stabilized via a different route, have (1) a unit cell size or dimension $a_o$ greater than about 24.45 angstroms, preferably between about 24.46 and 24.61 angstroms, and most preferably between about 24.52 and 24.59 angstroms and (2) a sorptive capacity for water vapor greater than about 15 weight percent at 25° C. and a p/p° value of 0.10, preferably greater than 18 weight percent, and usually between about 18 and 25 weight percent. As used herein, "p/p°" represent the water vapor partial pressure to which the zeolite is exposed divided by the water vapor partial pressure at 25° C. The overall silica-to-alumina mole ratio of these modified Y zeolites generally ranges between 5.0 and 6.0, typically between about 5.4 and 5.9. Examples of preferred steam stabilized Y zeolites include LZY-82 or Y-82 zeolite and LZY-84 or Y-84 zeolite sold by UOP, CP300-56 zeolite sold by the PQ Corporation, and CBV-530 and CBV-531 zeolites sold by Conteka-BV.

The dealuminated Y zeolites that can be used as the starting molecular sieve for preparing the catalyst are Y zeolites which have been chemically treated with acids, salts, or chelating agents to increase their overall silica-to-alumina mole ratio. The preferred dealuminated Y zeolites are prepared by dealuminating Y zeolites having an overall silica-to-alumina mole ratio below about 6.0 and are described in detail in U.S. Pat. Nos. 4,503,023 and 4,711,770, the disclosures of which patents are hereby incorporated by reference in their entireties. A preferred group of such zeolites is known as LZ-210 zeolites, zeolitic aluminosilicate molecular sieves available from UOP. LZ-210 zeolites and other zeolites are conveniently prepared from a Y zeolite starting material in overall silica-to-alumina mole ratios between about 6.0 and about 20, although higher ratios are possible. Preferred LZ-210 zeolites have an overall silica-to-alumina mole ratio of about 6.1 to about 16. Typically, the unit cell size is at or below 24.65 angstroms and will normally range between about 24.40 and about 24.60 angstroms. LZ-210 zeolites having an overall silica-to-alumina mole ratio below 20 generally have a sorptive capacity for water vapor of at least 20 weight percent based on the anhydrous weight of the zeolite at 25° C. and 4.6 millimeters mercury water capacity at 100 millimeters C. will be sorptive at least 25 weight percent. In general, LZ-210 zeolites are prepared by treating Y zeolites with an aqueous solution of a fluorosilicate salt, preferably a solution of ammonium hexafluorosilicate.

Ultrahydrophobic zeolites which can be used as a component of the catalyst of the invention are modified Y zeolites having a unit cell size between about 24.20 and about 24.45 angstroms, preferably between about 24.20 and 24.39 angstroms, most preferably between about 24.20 and 24.35 angstroms, and a sorptive capacity for water vapor less than about 5 weight percent, preferably less than about 4 weight percent, of the zeolite at 25° C. and a p/p° value of 0.10 . The zeolites are the same or similar to the UHP-Y zeolites disclosed in U.S. Pat. No. 4,401,556 and U.K. Patent 2,014,970 published on June 29, 1982, the disclosures of which patents are hereby incorporated by reference in their entireties. According to these references, a UHP-Y zeolite is defined as a zeolite having a silica-to-alumina mole ratio of from 4.5 to 35, the essential X-ray powder diffraction pattern of zeolite Y, an ion exchange capacity of not greater than 0.070, a unit cell size from 24.20 to 24.45 angstroms, a surface area of at least 350 square meters per gram (BET), a sorptive capacity for water vapor less than 5 weight percent at 25° C. and a p/p° value of 0.10, and a Residual Butanol Test Value of not more than 0.4 weight percent. The Residual Butanol Test is a measure of the adsorptive selectivity of zeolite adsorbents for relatively nonpolar organic molecules under conditions in which there is active competition between water and less polar molecules for adsorption on the zeolite. The test procedure is described in detail in the above-identified patents.

Preferably, the ultrahydrophobic zeolite has a silica-to-alumina mole ratio between about 4.5 and 9, the essential X-ray powder diffraction pattern of zeolite Y, an ion exchange capacity of not greater than 0.070, and a Residual Butanol Test Value of not more than 0.4 weight percent. More preferably, the ultrahydrophobic zeolite is LZ-10 zeolite, a modified Y zeolite having a silica-to-alumina mole ratio between about 4.5 and about 6.0, a surface area between about 500 and 700 square meters per gram, a unit cell size between about 24.20 and 24.35 angstroms, and a sorptive capacity for water vapor less than about 5 percent by weight of the zeolite at 25° C. and a p/p° value of 0.10.

Before the molecular sieve to be utilized in the catalyst of the invention is combined with the porous, inorganic refractory oxide which will serve as the binder or matrix for the sieve, it will normally be catalytically active for alkylation and transalkylation reactions and contain ammonium ions. The activity of the molecular sieve is typically dependent on the amount of alkali metal associated with the acid sites of the sieve. Some of the molecular sieves that are suitable for use in the catalyst, such as the steam-stabilized Y zeolites described above, will already contain ammonium ions and have such a low concentration of sodium or other alkali metal cations that they will possess the requisite activity and can be combined directly with the refractory oxide component. If, however, the molecular sieve contains a high concentration of sodium or other alkali metal cations, it is normally desirable to exchange the sieve with ammonium ions to lower the alkali metal content and provide the sieve with ammonium ions.

The ammonium ion exchange is carried out by mixing the molecular sieve with an aqueous solution containing a dissolved ammonium salt, such as ammonium nitrate, ammonium sulfate, ammonium chloride and the like. The resulting slurry is stirred for between about 1 and about 5 hours at temperatures above ambient but less than 100° C. If sodium levels below 0.50 weight percent are desired, the ion exchange procedure will normally have to be repeated at least once. Typically, the ion exchange procedure will be repeated at least twice and occasionally several times to reduce the sodium or other alkali metal content preferably to below 0.2 weight percent, calculated as $Na_2O$.

The molecular sieve possessing alkylation and/or transalkylation activity is combined with one or more inorganic refractory oxide components, or precursors thereof, such as alumina, silica, titania, magnesia, zirconia, beryllia, a naturally occurring clay, such as kaolin, hectorite, sepiolite, attapulgite, montmorillonite or beidellite, silica-alumina, silica-magnesia, silica-titania, mixtures thereof and other such combinations and the like. Examples of precursors that may be used include peptized alumina, alumina gel, hydrated alumina, silica-alumina hydrogels and silica sols. The inorganic refractory oxide components or precursors thereof, which serve as a matrix for the molecular sieve, are typically amorphous and are usually mixed or comulled with the molecular sieve in amounts such that the final catalyst mixture will comprise (1) between about 50 and about 95 weight percent molecular sieve, preferably between about 70 and 95 weight percent, and (2) between about 5 and 50 weight percent of one or more inorganic refractory oxides, preferably between about 5 and 30 weight percent.

The desired inorganic refractory oxide component(s) or precursor(s) thereof is typically mulled, normally in the form of a powder, with the ammonium-exchanged molecular sieve particles. After mulling, the mixture is extruded through a die having openings of a cross sectional size and shape desired in the final catalyst particles. The catalyst may be made in any shape extrudates including, among others, extrudates having the cross section of a circle or a three-leaf clover similar to the shape shown in FIGS. 8 and 8A of U.S. Pat. No. 4,028,227, the disclosure of which is hereby incorporated by reference in its entirety. Normally, the length of the catalyst particles ranges between about 0.10 and 0.50 inch and the diameter between about 0.03 and 0.08 inch. The preferred sizes of the catalyst particles are described in detail in U.S. Pat. No. 4,185,040, the disclosure of which is hereby incorporated by reference in its entirety. After the extruded catalyst has been broken into particles of the desired length, the catalyst particles are dried and subjected to calcination at an elevated temperature, normally between about 600° F. and about 1600° F., preferably between about 700° F. and about 1200° F., to produce a catalyst of high crushing strength.

It has typically been the practice in the art of making molecular sieve-containing catalysts of any type to carry out the final calcination step at temperatures that are sufficiently high to not only provide the high crushing strength required of the catalyst but also to decompose substantially all of the ammonium ions in the molecular sieve into ammonia and hydrogen ions, thereby activating the catalyst by removing ammonia which neutralizes the active acid sites in the molecular sieve. The use of these high calcination temperatures also drives off substantially all of the water present and typically results in a substantially dry catalyst. It has now been surprisingly found that the life of an alkylation or transalkylation catalyst prepared as described above is decreased when the catalyst is substantially dry. In order to maintain a relatively long catalyst life, it has been found that the water content of the fresh catalyst must be above about 3.5 weight percent before it is used in alkylation and/or transalkylation processes.

In view of the above and in accordance with the invention, the calcined catalyst particles are hydrated so they contain water in an amount above about 3.5 weight percent. Typically, the hydration is carried out such that the hydrated catalyst particles will contain greater than about 4.0 weight percent water, preferably more than about 5.0 weight percent, more preferably greater than about 6.0 weight percent, and most preferably greater than about 7.0 weight percent. Typically, the amount of water in the catalyst will range between about 4.0 and about 25 weight percent, preferably between about 5.0 and about 15 weight percent, and more preferably between about 5.0 and 10 weight percent.

As mentioned previously, the discovery that the water level in a molecular sieve-based alkylation or transalkylation catalyst beneficially affects the life of the catalyst is quite surprising in light of the conventional practice of driving off substantially all of the water during calcination. Although the invention is not limited to any theory of operation, it is believed that this surprising phenomenon is due to the extra water preferentially adsorbing onto some of the active sites in the molecular sieve and thereby deactivating them so they do not crack, during process start-up, the molecules of the reactant which undergoes alkylation or transalkylation once process start-up is completed. During start-up, this reactant is introduced into the alkylation or transalkylation reaction zone in contact with the catalyst, and the temperature in the reaction zone is slowly increased to reaction temperature before the alkylating or transalkylating agent is introduced. During this initial heat-up period, the water content of the catalyst is determined by the equilibrium between the catalyst, the reactant first introduced into the reaction zone, and the amount of water in the reaction zone, if any, at temperatures in the reaction zone. If the catalyst contains less than its equilibrium amount of water at any time during the initial heat-up, it is believed the more active sites in the molecular sieve tend to promote cracking of the molecules of the first introduced reactant into materials that react with benzene or condense to form larger molecules which deposit on the catalyst, thereby poisoning active sites and decreasing catalyst life. It is believed that the presence of water in excess of equilibrium amounts at any temperature during the heat-up step that is above the temperature at which the first introduced reactant undergoes cracking will deactivate cracking sites in the catalyst and thereby decrease the formation during start-up of larger molecules which poison the catalyst and thereby significantly reduce its life.

In order to accomplish hydration of the catalyst particles so they contain the desired amount of water, the calcined particles may be sprayed with water. Normally, this procedure is carried out by passing the calcined catalyst particles on a moving belt under a series of spray or fog nozzles designed to finely disperse the water. The molecular sieve portion of the catalyst is highly hydrophilic and will quickly absorb the water. The level of hydration is controlled by adjusting the rate at which the catalyst passes under the nozzles or the rate of water flow through the nozzles. Usually, the temperature during the hydration step is maintained between about 5° C. and about 100° C. The water content of the catalyst is calculated by measuring weight loss on ignition (LOI), which is normally determined by calculating the weight loss after heating for 2 hours at 1000° C., and then subtracting the amount of weight loss due to ammonium ion decomposition into ammonia. Since a catalyst containing water in excess of the desired amount, i.e., greater than the equilibrium amount of water the catalyst will contain at any time during process start-up, will lose that water once equilibrium is established during start-up, the hydration step can be carried out to give the catalyst any amount of water as long as it is equal to or exceeds the equilibrium amount.

As is discussed in U.S. Pat. No. 5,036,033, which patent is hereby incorporated by reference in its entirety, it has been found that a minimum concentration of at least 250 ppmw ammonium ions, calculated as $(NH_4)_2O$ on a volatiles-free basis, in molecular sieve-based alkylation and transalkylation catalysts helps to maintain high levels of selectivity for desired products. Thus, the catalyst of the invention will typically contain, in addition to greater than 3.5 weight percent water, more than this minimum amount of ammonium ions, preferably between about 2,000 and 8,000 ppmw. The desired ammonium ion concentration in the catalyst is achieved by controlling the time and temperature conditions at which the extruded catalyst particles are calcined. In some cases, calcination at lower temperatures will provide not only the desired crush strength and ammonium ion concentration, but will also leave the required amount of water in the catalyst and thereby make it unnecessary to carry out a separate hydration step. Thus, "hydrating" and "hydration" as used herein not only mean a separate step in which water is added to the catalyst after calcination but also encompass a calcination step carried out under conditions such that the desired amount of water remains on the catalyst particles.

The hydration procedure described above is part of the actual process of making the catalyst of the invention at the manufacturing plant. It will be understood, however, that procedures other than that described above can be used to hydrate the catalyst either in the manufacturing plant at the time the catalyst is made or at some other time at the manufacturing plant or elsewhere. For example, the extruded catalyst particles can be hydrated in-situ in the alkylation or transalkylation reactor by passing a water-containing gas, such as humid air, or a water-containing reactant, such as wet liquid benzene, over the catalyst at relatively low temperatures until the catalyst contains the desired amount of water. Also, the catalyst particles can be stored at the manufacturing plant or elsewhere so that they are in contact with the surrounding air until the desired amount of water has been absorbed.

Catalysts prepared as described above are useful in a wide variety of alkylation and transalkylation processes in which an alkylated organic compound is produced by contacting an organic feedstock with an organic reactant in the presence of the catalyst. Alkylation can be broadly defined as the addition or insertion of an alkyl group into a molecule. Thus, alkylation reactions are diverse in nature. In transalkylation reactions, which are closely related to alkylation reactions, an alkyl group moves from one molecule to another. The catalyst of the invention is effective in catalyzing both alkylation and transalkylation reactions while maintaining a relatively long life.

In general, the catalyst of the invention can be used to catalyze the alkylation of saturated and unsaturated, branched and straight chain, aliphatic compounds, monocyclic and polycyclic aromatic compounds and substituted derivatives of such monocyclic and polycyclic compounds, and cycloaliphatic compounds. The alkylating agent used may be any compound capable of reacting with the compound to be alkylated. Typical alkylating agents include alkenes or olefins, alcohols such as methanol, alkylhalides, esters, ethers, aldehydes, ketones, amines, and thiocyanates. The catalyst of the invention can also be used in any transalkylation process in which a polyalkylated organic compound is converted into a lesser alkylated or nonalkylated organic compound by transferring one or more alkyl groups from the polyalkylated compound to a similar compound containing fewer alkyl groups.

Although the catalyst of the invention can be used in any transalkylation or alkylation process, its preferable uses are in processes for the alkylation of aromatic hydrocarbons with $C_2$-$C_4$ olefins to produce monoalkyl aromatic compounds and in the transalkylation of aromatic compounds to produce monoalkyl aromatic compounds. Normally, the alkylating agent used in such alkylation processes will be ethylene, propylene, isobutene or n-butene. Usually a monoalkylated product is desired, but polyalkylated products can also be produced by, for instance, using toluene as the aromatic compound and ethylene as the alkylating agent.

The catalyst of the invention is preferably used in alkylation and transalkylation reactions to make cumene from benzene and propylene and to make ethylbenzene from benzene and ethylene. Cumene is commonly used as an intermediate to produce phenol while ethylbenzene is primarily used as an intermediate in producing styrene. FIG. 1 in the drawing illustrates a specific embodiment of the process of the invention in which the catalyst of the invention is utilized both as an alkylation and a transalkylation catalyst. This embodiment of the invention can be used to produce either cumene (isopropylbenzene) or ethylbenzene depending on whether the alkylating agent utilized is propylene or ethylene.

To start the process up, benzene is passed at ambient temperature through lines 12 and 14, preheater 20 and line 22 into adiabatic alkylation reactor 24 which may contain one or more beds of the catalyst of the invention. It is normally desired that the benzene introduced into reactor 24 contain a small amount of water in order to maintain catalyst stability during the alkylation process. Thus, the benzene normally contains between about 20 and 3000 ppmw water, preferably between about 150 and 1500, and more preferably between about 300 and 1000 ppmw water. The water-laden benzene is circulated at ambient temperature through lines 26 and 28, heat exchanger 32, line 34, distillation column 36 and line 38 into lines 16 and 18. A portion of this benzene is recycled to reactor 24 through lines 14 and 22, while the remaining amount is passed through lines 18 and 54, preheater 56 and line 58 into transalkylation reactor 60 which also contains one or more beds of the catalyst of the invention. From reactor 60, the benzene is passed through lines 62 and 28, heat exchanger 32, and line 34 to distillation column 36.

Once the water-containing benzene is circulating at ambient temperature through the process system as described above, the temperature of the benzene is slowly increased toward alkylation and transalkylation temperatures by use of preheaters 20 and 56, respectively. The catalysts in both reactors 24 and 60 contain a sufficient amount of water to moderate their cracking activity with respect to benzene as the temperatures in the reactors are raised to reaction levels. Thus, excessive cracking of the benzene into products that react with benzene and condense to form larger molecules which deposit on the catalysts, thereby decreasing their life, is avoided. The catalysts contain sufficient amounts of water so that their water content is equal to or greater than the equilibrium water content of the catalysts at any temperature during the period of heat up, which temperature exceeds that at which the benzene begins to crack. Water levels in the catalysts or above 3.5 weight percent, preferably between 4.0 and 25 weight percent, are usually sufficient.

If the catalysts do not contain a sufficient amount of water when first loaded into reactors 24 and 60, they can be hydrated in-situ prior to raising the beds to reaction temperature. This hydration can be accomplished by passing humid air through the beds or contacting the beds with the water-containing benzene at temperatures below which benzene cracks for a period of time sufficient for the catalyst to absorb the required amount of water.

Once reactors 24 and 60 have been raised to operating temperatures while circulating hot benzene, ethylene or propylene, depending on the desired product, is introduced into the system through line 10. The rate of introduction is slowly increased over a period of several days until design capacity is reached.

When the process is utilized to produce ethylbenzene, ethylene is passed through line 10 into line 14 where it is mixed with makeup benzene introduced into line 14 through line 12 and recycled benzene introduced into line 14 through line 16. The resultant mixture of ethylene, makeup benzene and recycled benzene is passed through line 14 into preheater 20 and then through line 22 into alkylation reactor 24. In the upstream portion of the catalyst bed in the alkylation reactor, ethylene reacts with benzene to produce ethylbenzene and polyalkylated aromatic compounds such as di- and triethylbenzenes. In the downstream part of the reactor, these polyalkylated benzenes undergo transalkylation by reacting with benzene to form additional ethylbenzene. The temperature in preheater 20 is controlled, depending upon the feed composition, to yield the desired maximum temperature in the alkylation reactor. Typically, the temperature in the alkylation reactor is between about 200° F. and 900° F., preferably between about 300° F. and 600° F., and is sufficiently low that ammonium ions in the catalyst are not decomposed and the formation of xylene is minimized. The pressure utilized in the reactor ranges between about 150 p.s.i.g. and 2000 p.s.i.g., preferably between about 300 p.s.i.g. and 1500 p.s.i.g. The weight hourly space velocity typically ranges between about 2 and 2000 reciprocal hours, preferably between about 4 and 100 reciprocal hours. The mole ratio of benzene to ethylene used typically ranges between about 1.0 and 100, preferably between about 4 and 40. The conditions of temperature and pressure are preferably correlated so that a liquid phase is present in the reactor. An excess of benzene is utilized in order to minimize the formation of oligomers and polymers of the alkylating agent, and undesired polyalkylated and other unwanted compounds.

The effluent from reactor 24 contains, among other compounds, ethylbenzene, unreacted benzene, diethylbenzene, triethylbenzene, n-propylbenzene, ethylbenzene and other aromatic compounds. This mixture is withdrawn from alkylation reactor 24 through line 26, depressured, and passed into line 28 where it is mixed with a recycle stream containing ethylbenzene which is introduced into line 28 through line 62. The mixture in line 28 is then passed into heat exchanger 32 where the mixture is cooled to distillation temperature. The cooled mixture is then passed through line 34 into distillation column 36 where unreacted benzene is taken overhead via line 38 and recycled in part to alkylation reactor 24 via lines 16, 14 and 22. Water is removed from the top of column 36 to prevent its build up in the process flow system.

The bottoms product from distillation column 36, which comprises ethylbenzene, diethylbenzene and other benzene-derived impurities, is passed through line 40 to distillation column 42 from which the desired product ethylbenzene is recovered overhead through line 44. The bottoms product from column 42 is passed through line 46 into distillation column 48 wherein diethylbenzene is removed overhead through line 50 while a bottoms fraction comprising high boiling undesirable by-products is removed from the distillation column through line 52 to prevent build up of such compounds in the system.

The overhead stream from distillation column 48 is passed through line 50, mixed with benzene withdrawn overhead of distillation column 36 through lines 38 and 18, and passed through line 54 into preheater 56 and then through line 58 into transalkylation reactor 60. Here, the mixture of diethylbenzene and benzene is passed over the catalyst of the invention under conditions such that transalkylation occurs, i.e., ethyl groups are transferred from the diethylbenzene to the benzene to form additional ethylbenzene, which is the desired product from this embodiment of the invention. The transalkylation reactor is normally operated at a temperature between about 350° F. and about 650° F., preferably between about 400° F. to about 600° F., such that at least some of the reactants are present in the liquid phase. The pressure in the transalkylation reactor typically ranges between about 150 p.s.i.g. and about 2000 p.s.i.g., preferably between about 300 p s.i.g. and 1500 p.s.i.g. The weight hourly space velocity normally ranges from about 0.5 to 50 reciprocal hours, preferably between about 1 and 15 reciprocal hours. The mole ratio of benzene to diethylbenzene introduced into the reactor is generally between about 1 and about 50, preferably between about 5 and about 40.

The effluent from transalkylation reactor 60 is withdrawn through line 62 and passed to line 28 where it is mixed with the bottoms from alkylation reactor 24 and subsequently passed through distillation column 36 to distillation column 42 for recovery of the additional ethylbenzene produced in the transalkylation reactor.

It will be understood that the flow scheme set forth in FIG. 1 can be used to produce cumene as a desired product by substituting propylene for the ethylene introduced into the process through line 10. When this is done and conditions in the process units are adjusted appropriately, cumene instead of ethylbenzene is recovered overhead of distillation column 42 through line 44 and diisopropylbenzene and triisopropylbenzene are passed through lines 54 and 58 into transalkylation reactor 60 where they are converted via reaction with benzene into additional cumene product.

In the process flow scheme shown in FIG. 1 and described above, reactants are passed downwardly through a single alkylation reactor 24, which is depicted as containing three beds of the catalyst of the invention, and through a single transalkylation reactor 60, which is shown as containing only one bed of the catalyst of the invention. It will be understood that alternative embodiments of the invention include passing the reactants upwardly through both reactors, using more beds in each reactor or fewer beds in the alkylation reactor, employing more than one reactor vessel for either alkylation or transalkylation, and using a transalkylation catalyst other than the catalyst of the invention in reactor 60. For example, in one embodiment of the invention for making ethylbenzene, benzene and ethylene are passed upwardly through two alkylation reactors containing two beds of the catalyst of the invention while benzene and diethylbenzene are passed upwardly through a single transalkylation reactor containing three separate beds of the catalyst of the invention or another transalkylation catalyst. Although the process flow scheme depicted in FIG. 1 shows ethylene being introduced into the system in one location upstream of preheater 20, it will be understood that the ethylene can be injected between preheater 20 and alkylation reactor 24 and, in addition, between the beds of catalyst in reactor 24.

The nature and objects of the invention are further illustrated by the following examples which are provided for illustrative purposes only and not to limit the invention as defined by the claims. Example 1 demonstrates that a hydrated catalyst of the invention has significantly less cracking activity for benzene than an unhydrated catalyst. Example 2 shows that a hydrated catalyst of the invention has a substantially increased life when used to alkylate benzene with ethylene.

EXAMPLE 1

A catalyst was prepared by mulling a mixture of (1) LZY-82 zeolite, a the steam-stabilized, modified Y zeolite, and (2) Catapal alumina that had been peptized with nitric acid. The mulled mixture was extruded through a clover leaf-shaped die, dried and calcined in air. The finished catalyst contained about 90 weight percent LZY-82 zeolite, about 10 weight percent alumina and about 4,000 ppmw ammonium ions, calculated as $(NH_4)_2O$ on a voltiles-free basis. The water content of the catalyst was measured by placing a sample of the catalyst in a muffle furnace and heating it at a 1,000° C. for two hours. After heating, the sample was again weighed. The difference in weights represents the loss on ignition (LOI) or the amount of volatiles present in the catalyst. Since the catalyst contained some ammonium ions which decomposed into ammonia when the catalyst was heated, the LOI measurement was adjusted to obtain the water content by subtracting the amount of ammonia generated. The water content calculated in this manner was about 3 weight percent based on the total weight of the catalyst. A portion of this catalyst was hydrated by spreading a single layer on a coarse screen supported above a table in a vent hood while air was freely circulated around the catalyst for at least two hours to ensure complete hydration. The dry and hydrated catalysts were stored in sealed bottles until used. The water content of the hydrated catalyst as measured by LOI and corrected for ammonium ion content was approximately 21 weight percent.

A 10 gram (dry basis) sample of the relatively dry catalyst, i.e., the catalyst containing 3 weight percent water, was supported on quartz chips in a fixed bed bench scale reactor having an inside diameter of 0.52 inches, which reactor was then placed in an electrically heated tube furnace. Reagent grade benzene that had been dried to contain 50 ppmw water was then passed downwardly through the reactor at a rate of 30 ml per hour and at a pressure of 600 p.s.i.g. No ethylene was introduced into the reactor. A thin travelling thermocouple in an external thermowell running the length of the reactor was used to measure temperatures. The temperature in the tube furnace was raised over a period of time to 480° F. The weight hourly space velocity was 2.7 reciprocal hours. Effluent from the reactor was collected at 12 hour intervals over a 4-day period. The samples collected were then inspected for color. All samples had approximately the same level of intense orange coloring. The orange product was analyzed by GC-MS methods and found to contain, in addition to benzene, cumene, alkylated benzenes, phenylnaphthalene, perylene, and 4- and 5-membered condensed aromatic compounds, i.e., polynuclear aromatics. These impurities were evidently formed by the reaction of benzene cracking products with one another, i.e., condensation, and with benzene.

The above-discussed experiment was repeated under identical conditions except that 10 grams (dry basis) of the hydrated catalyst were used in lieu of the dry catalyst and the product was collected at 12 hour intervals for a period of 12 days. The samples of the benzene exiting the reactor were then inspected, and all were found to have a light yellow coloration indicating the presence of substantially fewer impurities. It was thus concluded that much less benzene cracking had occurred over the hydrated catalyst than over the dry catalyst.

EXAMPLE 2

Figure 2:
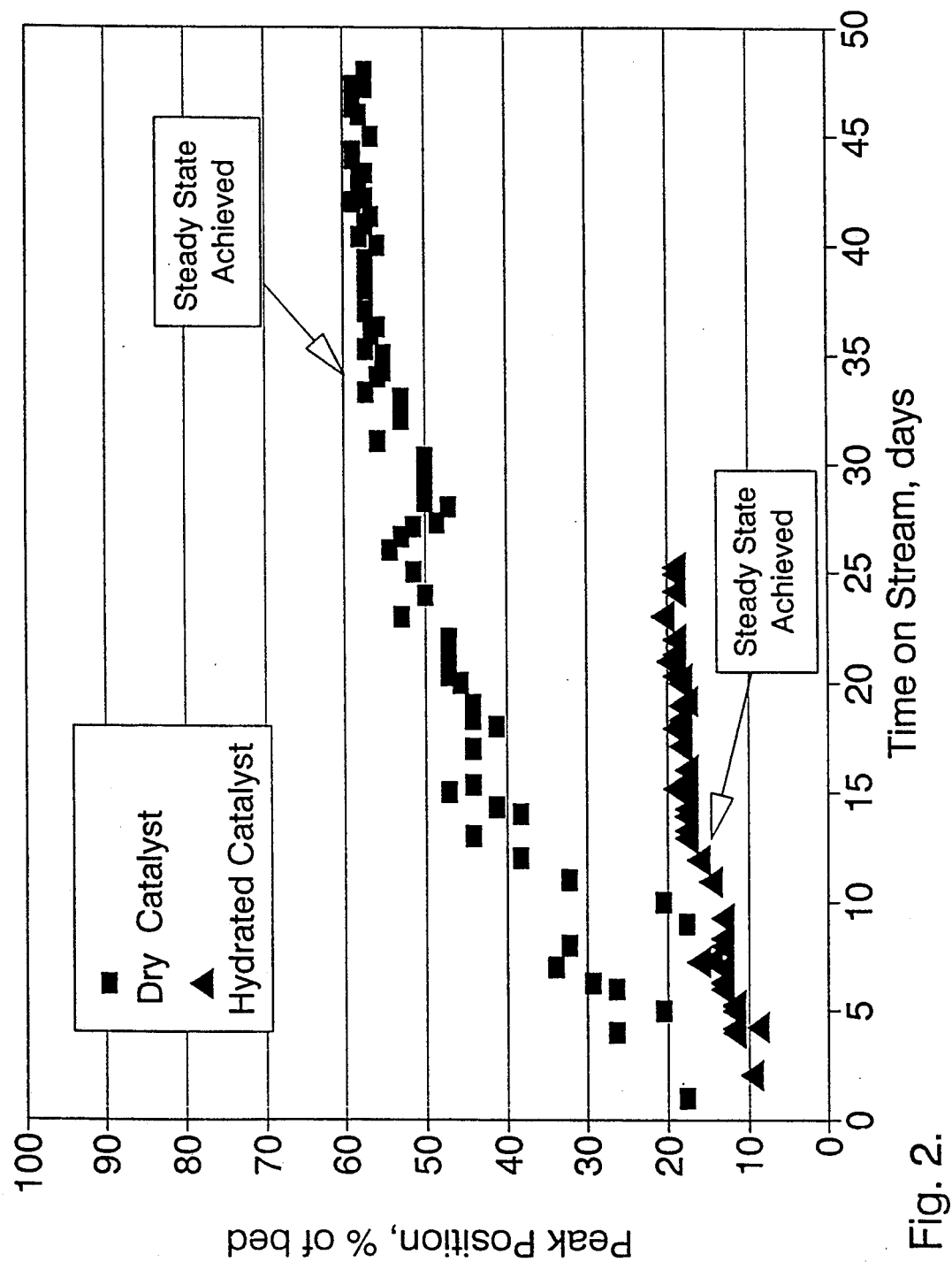
FIG. 2 is a plot which shows the position in beds of the catalyst of the invention and a catalyst containing less than the minimum required amount of water of the maximum or peak temperature for the reaction of benzene with ethylene to produce ethylbenzene versus days on stream.

The conclusions drawn from the results of Example 1 were confirmed in a pilot plant run in which the performance of the hydrated catalyst of Example 1 for alkylating benzene with ethylene was compared to that of the dry catalyst. Twenty-five grams (dry basis) of the catalyst of Example 1 containing 3 weight percent water were supported on quartz chips in a reactor which had an inside diameter of 0.68 inches and was surrounded by a constant temperature bath of fine sand fluidized with air. Reagent grade benzene, to which water was added so it contained between 2,000 and 3,000 ppmw water, was passed upwardly through the reactor at 600 p.s.i.g. and a rate of 243 grams per hour by means of a piston pump. The fluidized sand bath was then raised in temperature to between 450° and 467° F. at which time polymer grade ethylene was mixed with the benzene and passed upwardly through the fixed bed reactor at a rate of 7.3 grams per hour. The weight hourly space velocity was 10 reciprocal hours. The position of the reaction zone in the bed was determined by measuring temperatures at intervals as small as ⅛ inch through the bed using a thin travelling thermocouple in a central thermowell running the length of the reactor. Since the alkylation reaction is very exothermic and rapid, the temperature of the catalyst bed rises steeply at the inlet of the reactor and then drops off as heat is lost through the reactor walls to the constant temperature bath. The measured peak temperature of between 472° and 486° F. was used to mark the position of the reaction zone in the bed. Every day the position of the peak temperature was determined using the thermocouple and was plotted against time. These data are shown in FIG. 2.

As can be seen by the data in the figure, the position of the peak temperature in the bed changed rather rapidly over the first 15 days. The slope of the line represented by the data points is the rate of peak temperature travel, which rate is indicative of the length of the catalyst bed deactivated per day. After about 33 days, a steady state was reached where the rate of peak temperature travel remained fairly constant. About 57 percent of the catalyst bed was consumed when steady state was reached. The life of the catalyst can be predicted by dividing the length of the active catalyst bed remaining, i.e., 43 percent, by the rate of peak temperature travel and adding the time required to reach steady state, i.e. 33 days.

The above described pilot plan run was repeated using 25 grams (dry basis) of the hydrated catalyst, i.e., the catalyst containing about 21 weight percent water. All variables remained the same except that the benzene use contained only 800 ppmw water instead of between 2,000 and 3,000 ppmw. Again, the position of the peak temperature was measured daily and the results are shown in FIG. 2. As can be seen, the rate of peak temperature travel reached a steady state after about 13 days and only about 18 percent of the catalyst bed was consumed as compared to 57 percent after 33 days for the dry catalyst. Since the peak temperature moved through both beds at about the same rate after steady state was reached, which rate was very small, the predicted life of the hydrated catalyst, i.e., the length of active catalyst bed remaining divided by the rate of peak temperature travel plus the time to reach steady state, was about twice that of the dry catalyst. Such an increase in catalyst life has potentially large effects on the economics of the process since it allows the use of smaller amounts of reactants and less catalyst, which substantially cuts capital costs, and also results in the need for regenerating the catalyst fewer times during its total life time, which saves considerably on operation costs.

Although this invention has been primarily described in conjunction with the examples and by reference to embodiments thereof, it is evident that many alternatives, modifications and variations will be apparent to those skilled in the art in light of the foregoing description. Accordingly, it is intended to embrace within the invention all such alternatives, modifications and variations that fall within the spirit and scope of the appended claims.

We claim:

1. A catalyst composition substantially devoid of hydrogenation metal components comprising a crystalline molecular sieve having alkylation and/or transalkylation activity, wherein said catalyst composition contains greater than 3.5 weight percent water based on the total weight of said catalyst composition.

2. A catalyst composition as defined by claim 1 further comprising an inorganic refractory oxide component.

3. A catalyst composition as defined by claim 2 wherein said molecular sieve is a zeolitic molecular sieve.

4. A catalyst composition as defined by claim 3 wherein said zeolitic molecular sieve has a Constraint Index less than about 1.0.

5. A catalyst composition as defined by claim 3 wherein said zeolitic molecular sieve is a modified Y zeolite.

6. A catalyst composition as defined by claim 5 wherein said modified Y zeolite has a silica-to-alumina mole ratio less than about 20.

7. A catalyst composition as defined by claim 5 wherein said modified Y zeolite is a steam-stabilized Y zeolite.

8. A catalyst composition as defined by claim 7 wherein said steam-stabilized Y zeolite is prepared by the process comprising:
   (1) ammonium exchanging a sodium Y zeolite to a sodium content between about 0.6 and 5 weight percent, calculated as $Na_2O$,
   (2) calcining the ammonium-exchanged zeolite at a temperature between about 600° F. and 1650° F. in the presence of steam at a water vapor partial pressure of at least about 0.2 p.s.i.a. to reduce the unit cell size of said ammonium-exchanged zeolite to a value in the range between about 24.35 and about 24.65 angstroms, and
   (3) ammonium exchanging the steam-calcined zeolite to reduce the sodium content of the zeolite below about 0.6 weight percent, calculated as $Na_2O$.

9. A catalyst composition as defined by claim 8 wherein said steam-stabilized Y zeolite is LZY-82 zeolite or LZY-84 zeolite.

10. A catalyst composition as defined by claim 2 wherein said catalyst composition contains greater than about 4.0 weight percent water based on the total weight of said catalyst composition.

11. A catalyst composition as defined by claim 2 wherein said catalyst composition contains greater than about 5.0 weight percent water based on the total weight of said catalyst composition.

12. A catalyst composition as defined by claim 2 wherein said catalyst composition contains greater than about 6.0 weight percent water based on the total weight of said catalyst.

13. A catalyst composition as defined by claim 2 wherein said catalyst composition contains greater than about 7.0 weight percent water based on the total weight of said catalyst.

14. A catalyst composition as defined by claim 5 wherein said modified Y zeolite is a dealuminated Y zeolite.

15. A catalyst composition as defined by claim 5 wherein said modified Y zeolite is an ultrahydrophobic Y zeolite.

16. A catalyst composition as defined by claim 7 wherein said inorganic refractory oxide component is alumina.

17. A process for making an alkylation catalyst substantially devoid of hydrogenation metal components which process comprises:
   (a) extruding a mixture of at least one inorganic refractory oxide component and a crystalline molecular sieve having alkylation and/or transalkylation activity to form extrudates;
   (b) calcining said extrudates; and
   (c) hydrating said calcined extrudates so that the resultant catalyst contains greater than 3.5 weight percent water based on the total weight of the catalyst.

18. A process as defined by claim 17 wherein said molecular sieve is a steam-stabilized Y zeolite.

19. A process as defined by claim 18 wherein said steam-stabilized Y zeolite is LZY-82 zeolite or LZY-84 zeolite.

20. A process as defined by claim 17 wherein said inorganic refractory oxide component is alumina.

21. A process as defined by claim 17 wherein said calcined extrudates are hydrated under conditions such that the water content of said catalyst is between about 4.0 and about 25 weight percent based on the total weight of said catalyst.

22. A process as defined by claim 17 wherein said calcined extrudates are hydrated under conditions such that the water content of said catalyst is between about 5.0 and about 15 weight percent based on the total weight of said catalyst.

23. A catalyst composition as defined by claim 3 wherein said zeolithic molecular sieve is selected from the group consisting of zeolite Beta, zeolite L, zeolite Omega, mordenite, Y zeolites, X zeolites, fluorided Y zeolites, and modifications of such zeolites.

24. A catalyst composition as defined by claim 5 wherein said modified Y zeolite has an overall silica-to-alumina mole ratio between about 3.0 and about 6.0.

25. A catalyst composition as defined by claim 5 wherein said modified Y zeolite has an overall silica-to-alumina mole ratio between about 5.0 and about 6.0.

26. A catalyst composition as defined by claim 2 wherein said crystalline molecular sieve is a nonzeolitic molecular sieve selected from the group consisting of silicoaluminophosphates, metalloaluminophosphates, titanium silicates, galliosilicates, ferrosilicates, chromosilicates, borosilicates, pillared clays, delaminated clays, and crystalline silicas.

27. A catalyst composition as defined by claim 2 wherein said crystalline molecular sieve comprises a silicoaluminophosphate.

28. A catalyst composition as defined by claim 2 wherein said crystalline molecular sieve comprises silicalite.

29. A catalyst composition as defined by claim 2 containing between about 5.0 and about 15 weight percent water based on the total weight of said catalyst composition.

30. A catalyst composition as defined by claim 2 containing between 5.0 and 10 weight percent water based on the total weight of said catalyst composition.

31. A catalyst composition as defined by claim 2 containing between 4.5 and 9.5 weight percent water based on the total weight of said catalyst composition.

32. A process as defined by claim 17 wherein said calcined extrudates are hydrated under conditions such that the water content of said catalyst is between 4.5 and 9.5 weight percent based on the total weight of said catalyst.

33. A process as defined by claim 17 wherein said crystalline molecular sieve is a zeolitic molecular sieve selected from the group consisting of Y zeolites, fluorided Y zeolites, X zeolites, zeolite Beta, zeolite L, zeolite Omega, mordenite and modifications of such zeolites.

34. A process as defined by claim 17 wherein said crystalline molecular sieve is a nonzeolitic molecular sieve selected from the group consisting of silicoaluminophosphates, metalloaluminophosphates, titanium silicates, galliosilicates, ferrosilicates, chromosilicates, borosilicates, pillared clays, delaminated clays, and crystalline silicas.

35. A process as defined by claim 18 wherein said steam-stabilized Y zeolite has an overall silica-to-alumina mole ratio between about 5.0 and about 6.0.

36. A catalyst composition substantially devoid of hydrogenation metal components comprising a Y zeolite having alkylation and/or transalkylation activity and an inorganic refractory oxide component, wherein the finished catalyst composition contains between about 4.0 and 25 weight percent water based on the total weight of said catalyst composition.

37. A catalyst composition as defined by claim 36 wherein said Y zeolite is a modified Y zeolite selected from the group consisting of a steam-stabilized Y zeolite, a dealuminated Y zeolite, and an ultrahydrophobic Y zeolite.

38. A catalyst composition as defined by claim 36 wherein said Y zeolite is a steam-stabilized Y zeolite.

39. A catalyst composition as defined by claim 38 wherein said steam-stabilized Y zeolite has an overall silica-to-alumina mole ratio between about 3.0 and about 6.0.

40. A catalyst composition as defined by claim 38 wherein said steam-stabilized Y zeolite has an overall silica-to-alumina mole ratio between about 5.0 and about 6.0.

41. A catalyst composition as defined by claim 36 containing between about 5.0 and about 15 weight percent water based on the total weight of said catalyst composition.

42. A catalyst composition as defined by claim 36 containing between 4.5 and 9.5 weight percent water based on the total weight of said catalyst composition.

43. A catalyst composition as defined by claim 38 wherein said inorganic refractory oxide component comprises alumina and said catalyst contains between about 50 and 95 weight percent of said steam-stabilized Y zeolite.

44. A process for making an alkylation catalyst substantially devoid of hydrogenation metal components which comprises hydrating a finished catalyst containing a crystalline zeolitic molecular sieve having alkylation and/or transalkylation activity under conditions such that the resultant catalyst contains between about 4.0 and 25 weight percent water based on the total weight of the catalyst.

45. A process as defined by claim 44 wherein said finished catalyst is hydrated under conditions such that the water content of the catalyst is between 4.5 and 9.5 weight percent based on the total weight of the catalyst.

46. A process as defined by claim 44 wherein said crystalline zeolitic molecular sieve is a modified Y zeolite selected from the group consisting of a steam-stabilized Y zeolite, a dealuminated Y zeolite and an ultrahydrophobic Y zeolite.

47. A catalyst composition made in accordance with the process of claim 21.

48. A catalyst composition made in accordance with the process of claim 33.

49. A catalyst composition made in accordance with the process of claim 46.

50. A catalyst composition as defined by claim 36 containing between 5.0 and 10.0 weight percent water based on the total weight of said catalyst composition.

* * * * *